United States Patent [19]

Ehrl et al.

[11] Patent Number: 4,564,520
[45] Date of Patent: Jan. 14, 1986

[54] HAIR SHAMPOOS AND BODY CLEANSING AGENTS HAVING A CONTENT OF ALKYLSULFATOBETAINES

[75] Inventors: Winfried Ehrl, Neuötting; Alwin Reng, Kelkheim; Jochen M. Quack, Eppstein, all of Fed. Rep. of Germany

[73] Assignee: Hoechst Aktiengesellschaft, Fed. Rep. of Germany

[21] Appl. No.: 423,271

[22] Filed: Sep. 24, 1982

[30] Foreign Application Priority Data

Sep. 30, 1981 [DE] Fed. Rep. of Germany ....... 3138770

[51] Int. Cl.⁴ .................. A61K 7/06; C11D 1/18; C07C 143/00
[52] U.S. Cl. .................... 424/70; 252/545; 252/DIG. 5; 252/DIG. 13; 260/501.12
[58] Field of Search .............. 424/70; 252/545; 260/501.12

[56] References Cited

U.S. PATENT DOCUMENTS 3,929,678 12/1975 Laughlin et al. ............ 260/501.12
4,000,091 12/1976 Wentler ..................... 260/501.12
4,330,526 5/1982 Watanabe et al. ................ 424/70

*Primary Examiner*—Esther M. Kepplinger
*Assistant Examiner*—Shawn P. Foley
*Attorney, Agent, or Firm*—Connolly and Hutz

[57] ABSTRACT

Hair shampoo and body cleansing agent having a content of alkyl-sulfatobetaine of the formula

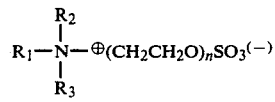

wherein $R_1$ is $C_8$–$C_{22}$alkyl or $C_8$–$C_{22}$alkenyl, preferably $C_{12}$–$C_{18}$alkyl, $R_2$ is $C_1$–$C_4$alkyl, preferably methyl, $R_3$ is $C_1$–$C_4$hydroxyalkyl or a group of the formula —$(CH_2CH_2O)_nH$ and n is an integer of from 1 to 10.

4 Claims, No Drawings

HAIR SHAMPOOS AND BODY CLEANSING AGENTS HAVING A CONTENT OF ALKYLSULFATOBETAINES

The human skin and human hair are generally cleansed by using aqueous surfactant-containing solutions. These surfactants are anionic, cationic, amphoteric or non-ionic compounds used alone or in combination. For example, frequently used cleansing agents are soaps, alkylsulfates, secondary alkanesulfonates, alkylether sulfates, α-olefinsulfonates, amine oxides, acylaminopolyglycol ether sulfates, fatty acid condensation products, sulfosuccinic acid esters, sarcosides, fatty alcohol polyglycol ethers. These cleansing agents primarily serve to remove foreign polluants and excess sebaceous matter from the surface of the body and the hair. The quantity of foam produced mechanically during the application of the aqueous surfactants during the cleansing operation is an indicator for the cleansing effect reached. The nature and the quantity of the foam produced depend greatly on the type of surfactant used. The same applies to the cleansing effect reached in each case. For example, anionic surfactants such as alkylsulfates, alkylbenzenesulfonates or soaps have a pronounced cleansing effect, which gives to the consumer the sense of having a "desiccated" surface of the skin, and which, especially in the case of hair shampoos, unfavorably affects the combability of the washed hair.

Trials have therefore been made to reduce said disadvantages by adding cationic polymers, alkylbetaines or alkylamidobetaines. Cationic polymer substances are characterized by a low water-solubility and very poor foaming properties and are difficult to synthesize, whereas alkylbetaines such as coconut dimethylbetaine have the disadvantage of a bad compatibility with the mucous membrane of the eye. Alkylamidobetaines, however, contain a great quantity of sodium chloride, as a by-product, which, during storage or processing, may frequently result in corrosion phenomena. Said surfactants, when used alone, finally have a moderate foaming behavior only and when used in conjunction with other surfactants, they do not decisively improve the wet and dry combability of human hair.

It has now been found that the alkylsulfatobetaines specified hereinafter do not have said disadvantages and that they permit the preparation of skin cleansing agents and hair shampoos which are characterized by very good foaming properties and which positively influence the handle of the hair and its combability. Said alkylsulfatobetaines, for example when processed to shampoos, foam baths, shower baths or cleansing agents for feminine hygiene or to other skin cleansing agents, do not provoke a "clammy" feel of the skin on application.

Subject of the present invention therefore are hair shampoos and body cleansing agents having a content of alkylsulfatobetaines of the formula

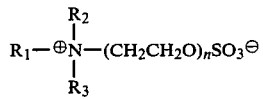

wherein $R_1$ is $C_8$–$C_{22}$ alkyl or $C_8$–$C_{22}$ alkenyl, preferably $C_{12}$–$C_{18}$ alkyl, $R_2$ is $C_1$–$C_4$ alkyl, preferably methyl, $R_3$ is $C_1$–$C_4$ hydroxyalkyl or a group of the formula —$(CH_2CH_2O)_nH$ and n is an integer of from 1 to 10.

The sulfatobetaines of the above formula are obtained according to known procedures by quaternizing an amine of the formula

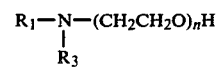

by introducing the radical $R_2$ followed by sulfatation of the resulting quaternary ammonium compound. Suitable quaternization agents are the compound known for this reaction such as alkylhalides, alkylsulfuric acid esters or alkylphosphoric acid esters. Methyl chloride and dimethyl sulfate are preferred. The reaction is carried out in a suitable solvent at boiling temperature. Suitable solvents are, for example, lower alcohols and acetonitrile.

Sulfatation takes place subsequently in the same solvent or in a different solvent at a temperature of from 0° to 60° C., preferably of 30° C. Suitable solvents for this reaction are, in addition to acetonitrile, halogenated hydrocarbons. Suitable sulfating agents are, for example, concentrated sulfuric acid, solutions of sulfur trioxide in sulfuric acid, and especially chlorosulfonic acid and sulfur trioxide. The quantity of sulfating agent is chosen such that only one sulfato group is introduced into the quaternary amine.

The alkylsulfatobetaines synthesized according to the aforesaid process are suitable for the manufacture of hair shampoos and body cleansing agents. The surfactants may be processed alone or in combination with other usual anionic, cationic, amphoteric and/or non-ionic surfactants. For example, they may be incorporated into hair shampoos, foam baths, face cleansing agents, shower baths, hand and foot cleansing agents, cleansing agents for feminine hygiene, and other special cosmetic cleansing agents.

The alkylsulfatobetaines are well compatible with most of the components used for said cosmetic cleansing agents. These components may be, for example, viscosity-improving substances such as cellulose ethers, electrolytes such as sodium chloride, magnesium chloride, ammonium chloride, or magnesium aluminum silicates, highly dispersed amorphous silicic acid, polyacrylamides or similar substances. Substances such as allantoin, anti-dandruff agents, preservatives, UV-absorbers, dyestuffs may moreover be incorporated into the alkylsulfatobetaine-containing cleansing preparations. Depending on the intended application field, the cleansing agents may be processed to give powders, gels or liquids. In the manufacture of the liquid products, further liquid components such as 1,2-propylene glycol, polyethylene glycols, glycerin, ethanol may be added in addition to water. The pH of said cleansing agents may be adjusted between 4 and 9, depending on the application purpose.

The feed quantities of the alkylsulfatobetaines are generally within the range of from 1 to 50%, preferably of from 5 to 20%, referred to the weight of the ready-to-use formulations. It is also possible to combine the alkylsulfatobetaines with other surface-active substances customarily used in cosmetic cleansing agents such as alkylsulfates, alkylether sulfates, soaps, carboxylic acid sarcosides, condensation products of carboxylic acid and proteins, sulfosuccinic acid esters, α-olefinsulfonates, secondary alkanesulfonates as well as with nonionic alcohol polyglycol-ethers or-esters.

The present invention will be illustrated by the following examples.

EXAMPLE 1

447 g (1.5 mols) of N,N-bis-hydroxyethyl-coconut-fatty-alkylamine and 300 ml of actonitrile are introduced into a 1 liter glass autoclave. The quantity of methyl chloride required is introduced portionwise under pressure at 80° C. The reaction is practically complete, when no more methyl chloride is absorbed. The reaction product contains 97.3% of the quaternized product.

The reaction product obtained is diluted with a further 500 ml of acetonitrile and introduced into a 4 liter three-necked flask provided with a stirrer, a dripping funnel, a reflux condenser and a thermometer. Next, 175 g (1.5 mols) of chlorosulfonic acid are added, while stirring, in a manner such that the temperature in the reaction vessel does not exceed 30° C. The batch is refluxed, while stirring, for one hour. The solvent is distilled off, the residue is absorbed by water to give a 30% solution of the compound of the formula

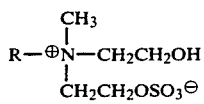

wherein R is coconut fatty alkyl.

EXAMPLE 2

745 g (2.5 mols) of N,N-bis-hydroxyethyl-coconut fatty-alkylamine are introduced into a 2 liter three-necked flask provided with a stirrer, a dripping funnel, a reflux condenser and a thermometer, and are dissolved in 500 ml of isopropanol. At 50°–60° C. 320 g of dimethyl sulfate (2.54 mols) are slowly dropped in, while stirring. The reaction mixture is left to stand for 2 hours at 60° C. to complete its reaction. The solvent is withdrawn on a rotary evaporator at 60° C. and in a water jet vacuum. The portion of quaternary compound is found to be 97%. The dry residue left upon quaternization is absorbed by 1,000 ml of acetonitrile and introduced into a 4 liter three-necked flask provided with a dripping funnel, a stirrer, a reflux condenser and a thermometer. 295 g (2.53 mols) of chloro-sulfonic acid are added, while stirring, in a manner such that the temperature in the reaction vessel does not exceed 30° C. The batch is refluxed for one hour while stirring, the solvent is distilled off on a rotary evaporator and the residue is absorbed by water to give a 30% solution of the compound of the formula

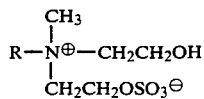

wherein R is coconut fatty alkyl.

The pH of the solution obtained is adjusted to 7 with sodium hydroxide solution. The solution is bleached with $H_2O_2$ (2% referred to the solid matter) to reduce its iodine color number from 3 to 1.

Analysis: $SO_4^{--} = 0.4\%$
Hydrolyzable $SO_4^{--} = 9.8\%$.

EXAMPLE 3

146 g (0.5 mol) of N,N-bis-hydroxyethyl-coconut-fatty-alkylamine are introduced into a 1 liter three-necked flask provided with a stirrer, a dripping funnel, a reflux condenser and a thermometer, are dissolved in 200 ml of acetonitrile and supplemented, while stirring, with 63 g (0.5 mol) of dimethyl sulfate, at 50°–60° C. The batch is left to stand for one hour at 60° C. to complete its reaction. To the reaction mixture obtained there are slowly added in a manner such that the temperature in the reaction vessel does not exceed 30° C., 58.3 g (0.5 mol) of chlorosulfonic acid and the batch is left to stand for two hours at 30° C. to complete its reaction, while slightly reducing the pressure in order to remove residual gaseous HCl.

The solvent is withdrawn on a rotary evaporator. The dry residue is absorbed by water to give a 30% solution and the pH of the solution is adjusted to 7 with sodium hydroxide solution. The solution is bleached with $H_2O_2$ (2% referred to the solid matter) to reduce its iodine color number from 4 to 1. The resulting sulfobetaine has the formula

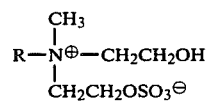

wherein R is coconut fatty alkyl.

EXAMPLE 4

422 g (1 mol) of N,N-bis-pentaoxyethylene-coconut-fatty-alkylamine in 400 ml of acetonitrile are introduced into a 1 liter three-necked flask provided with a stirrer, a dripping funnel, a reflux condenser and a thermometer, 126 g (1 mol) of dimethyl sulfate are dropped in, while stirring, at 50°–60° C. and the batch is left to stand for one hour at 60° C. to complete its reaction. To this reaction mixture there are slowly added in a manner such that the temperature in the reaction mixture does not exceed 30° C., 116.5 g (1 mol) of chlorosulfonic acid and the product is left to stand for two hours at 60° C. to complete its reaction, while slightly reducing the pressure in order to remove residual gaseous HCl. The solvent is withdrawn on a rotary evaporator. The dry residue is absorbed by water to give a 30% solution and its pH is adjusted to 7 with sodium hydroxide solution. By bleaching with $H_2O_2$ (2% referred to the solid matter) the iodine color number is reduced from 20 to 3. The resulting sulfobetaine has the formula

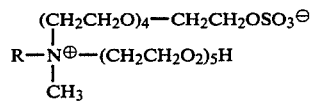

wherein R is coconut fatty alkyl.

EXAMPLE 5

500 g (0.78 mol) of N,N-bis-decaoxyethylene coconut-fatty-alkylamine are introduced into a 1 liter three-necked flask provided with a stirrer, a dripping funnel, a reflux condenser and a thermometer, are dissolved in 400 ml of acetonitrile and at 50°–60° C. 98 g (0.78 mol) of dimethyl sulfate are dropped in while stirring. The reaction mixture is left to stand for one hour at 60° C. to complete its reaction. 90.3 g (0.78 mol) of chlorosulfonic acid are slowly added dropwise to the reaction mixture in a manner such that the temperature in the reaction vessel does not exceed 30° C. and the batch is left to stand for two hours at 30° C. to complete its reaction. Gaseous HCl formed is removed under slightly reduced pressure. The solvent is withdrawn on a rotary evaporator. The dry residue is absorbed by water to give a 30% solution and the pH of the resultant solution is adjusted to 7 with sodium hydroxide solution. By bleaching with $H_2O_2$ (2% referred to the solid matter) the iodine color number of the solution is reduced from 8 to 3. The resultant sulfobetaine has the formula

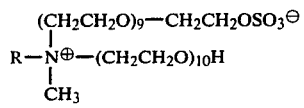

wherein R is coconut fatty alkyl.

EXAMPLE 6

460 g (1.28 mols) of N,N-bis-hydroxyethyl-coconut-fatty-alkylamine are introduced into a 1 liter three-necked flask provided with a stirrer, a dripping funnel, a reflux condenser and a thermometer, dissolved in 400 ml of acetonitrile and 161.3 g (1.28 mols) of dimethyl sulfate are added dropwise, while stirring, at 50°–60° C. 149.1 g (1.28 mols) of chlorosulfonic acid are added slowly to the quaternization mixture in a manner such that the temperature does not exceed 30° C. The batch is left to stand for 2 hours at 30° C. to complete its reaction, while applying a slight vacuum in order to remove residual gaseous HCl. The solvent is withdrawn on a rotary evaporator. The dry residue is absorbed by water to give a 30% solution and the pH of said solution is adjusted to 7 with sodium hydroxide solution. By bleaching with $H_2O_2$ (2% referred to the solid matter) the iodine color number of the solution is reduced from 12 to 2. The resultant sulfobetaine has the formula

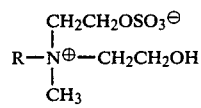

wherein R is coconut fatty alkyl.

The advantages obtained when using alkylsulfatobetaines in cosmetic hair shampoos and body cleansing agents become evident in the following tests:

1. Foaming behavior

The foaming behavior was determined according to the method of Ross-Miles (cf. S. J. Gohlke, "Die Bestimmung des Schaumvermögens von Detergentien nach Ross-Miles", Parfümerie und Kosmetik 45, 359–63 (1964) in water of 20° German hardness at a temperature of +43° C. As comparative substance there was used a fatty acid amidoalkylbetaine having the following composition:

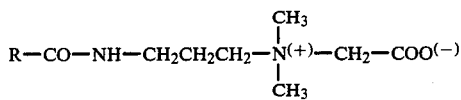

wherein R is $C_{12-14}$.

This type of betaine was compared with an alkylsulfatobetaine having the formula

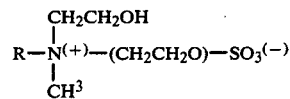

wherein R is $C_{12-14}$. The foam values listed in the following table were obtained. The foaming behavior of the alkylsulfatobetaine to be used according to the invention was better in both cases.

| Concentration in % | Foam height in mm Alkylsulfatobetaine | Alkylamidobetaine |
| --- | --- | --- |
| 0.002 | 30 | 20 |
| 0.006 | 60 | 50 |
| 0.03 | 150 | 135 |
| 0.1 | 210 | 180 |
| 0.3 | 240 | 200 |
| 1 | 250 | 225 |

2. Feel of the skin

The "feel of the skin" after the cleansing operation was tested by the following method:

In each case 10 g of surfactant were dissolved in 90 g of distilled water, while stirring. 10 Neutral test persons washed their hands for 25 seconds using 20 g of said solution in each case and rinsed their hands using 300 ml of tap water for 35 seconds. The hands were dried with a clean cotton towel and the feel of the skin after drying was assessed subjectively. The following results were obtained:

Alkylsulfatobetaine: soft, agreeable feel of the skin according to Example 1,

Sodium laurylsulfate: very clammy disagreeable feel of the skin,

Alkyldiglycol ether sulfate/sodium salt: clammy, disagreeable feel of the skin,

The assessments were repeated 5 minutes later to obtain the following results:

Alkysulfatobetaine: soft, agreeable feel of the skin,

Sodium laurylsulfate: dry, desiccated skin, which is "strained"

Alkyl diglycol ether sulfate/sodium salt: rought, dry feel of the skin, which latter is slightly "strained".

3. Combability of the hair

Strands of hair of Central Europeans of 15 cm length and of 1.5 cm diameter were washed with the aqueous solution to be tested containing 15% of surfactant and were rinsed with tap water of 35° C. Subsequently, the combability of the wet hair, the handle of the hair and its consistency were assessed. The results are summarized in the following table.

| Surfactant | Wet combability | Handle of the hair | Dry combability |
| --- | --- | --- | --- |
| Alkylsulfatobetaine according to Example 1 | very good | soft, smooth | very good |
| Laurylsulfate sodium salt | very good | hard, rough | poor |
| Lauryldiglycol ether sulfate | poor | hard, rough | moderate |

-continued

| Surfactant | Wet combability | Handle of the hair | Dry combability |
|---|---|---|---|
| sodium salt | | | 5 |

4. Physical and chemical stability to storage

Samples of a 1% aqueous solution of the compounds of Examples 1–6 were stored for 5 months at +25° C. and at +40° C. After 14 days the pH and the iodine color numbers were measured electrometrically according to the German industrial standard DIN No. 6162. Significant alterations of the pH and of the color were not observed. The following examples serve to illustrate the application possibilities of the alkylsulfatobetaines when used in hair shampoos and body cleansing agents. Quantities and percentages in the examples are by weight, unless otherwise stated.

EXAMPLE 1

| 1. Hair shampoo having a conditioning effect | |
|---|---|
| Alkylsulfatobetaine sodium salt according to Example 1 | 15.0% |
| Hydroxyethylcellulose ether | 1.2% |
| Perfume oil | 0.3% |
| Formaldehyde | 0.05% |
| Water the remainder to | 100%. |
| 2. Hair shampoo having a mild cleansing effect | |
| Alkylsulfatobetaine sodium salt according to Example 1 | 7.0% |
| Acylaminopolyglycol ether-sulfate-triethanolamine salt | 7.0% |
| Coconut-fatty acid ethanolamide | 2.0% |
| Triethylene glycol distearate | 1.0% |
| Sodium chloride | 2.0% |
| Perfume oil | 0.3% |
| Formaldehyde | 0.05% |
| Water the remainder to | 100.0% |
| 3. Acid shampoo | |
| Alkylsulfatobetaine sodium salt according to Example 1 | 10% |
| Lauryldimethyl-amine oxide | 5.0% |
| Citric acid | 0.4% |
| Perfume oil | 0.2% |
| Preservative, Dyestuffs and water the remainder to | 100%. |
| 4. Shampoo for dry hair | |
| Alkylsulfatobetaine-sodium salt according to Example 1 | 12.0% |
| Pentaoxethylammonium chloride | 1.0% |
| Alkyltriglycol -ether sulfate-sodium salt | 3.0% |
| Ethylene glycol monostearate | 0.7% |
| Polyethylene glycol-6000-distearate | 4.0% |
| Water, preservatives, dyestuffs the remainder to | 100%. |
| 5. Anti-dandruff shampoo | |
| Alkylsulfatobetaine sodium salt according to Example 5 | 12.0% |
| Palm nut fatty acid methyltauride sodium salt | 15.0% |
| Stearic acid methyltauride sodium salt | 6.0% |
| Lauroyl sarcoside sodium salt | 2.0% |
| 2-Mercaptopyridene-N—oxide zinc salt | 0.5% |
| Perfume oil | 0.3% |
| Water the remainder to | 100%. |
| 6. Shower bath | |
| Alkylsulfatobetaine according to Example 1 | 10.0% |
| Lauryltriglycol ether-sulfosuccinate-disodium salt | 5.0% |
| Hydroxyethylcellulose ether | 1.6% |
| Perfume oil | 0.2% |

-continued

| | | |
|---|---|---|
| Coconut fatty acid-mono-ethanolamide | | 1.5% |
| Imidazolidinyl urea | | 0.3% |
| Water the remainder to | | 100%. |
| 7. Hand cleansing agent | | |
| Alkylsulfatobetaine sodium salt according to Example 3 | | 6.0% |
| Secondary alkanesulfonate sodium salt | | 4.0% |
| Coconut fatty acid isothionate sodium salt | | 3.0% |
| Coconut fatty acid diethanolamide | | 2.0% |
| 2,4,4'-Trichloro-2-hydroxydiphenyl ether | | 0.1% |
| Lactic acid | | 0.15% |
| Water the remainder to | | 100%. |
| 8. Foot cleansing agent | | |
| Alkylsulfatobetaine according to Example 1 | | 8.0% |
| Laurylsulfate sodium salt | | 3.0% |
| Lauryl decaglycol ether | | 2.0% |
| Undecylenic acid monoethanolamide | | 3.0% |
| Formaldehyde | | 0.05% |
| Water the remainder to | | 100%. |
| 9. Cleansing agent for feminine hygiene | | |
| Alkylsulfatobetaine according to Example 1 | | 6.0% |
| Coconut ethylcycloimidino-1-hydroxy-3-ethylsodium alcoholate-2-methyl-sodium carboxylate | | 5.0% |
| Citric acid | | 0.3% |
| Alkyltriglycol ether sulfate-triethanolamine salt | | 3.0% |
| 3,4,4'-Trichlorocarbanilide | | 0.2%. |
| 10. Foam bath | | |
| Alkylsulfatobetaine sodium salt according to Example 6 | | 10.0% |
| Coconut diglycol ether sulfate sodium salt | | 30.0% |
| Secondary alkanesulfonate | | 10.0% |
| Oleic acid diethanolamide | | 1.0% |
| Perfume oil | | 1.0% |
| Sodium chloride | | 2.5% |
| Water the remainder to | | 100%. |

What is claimed is:

1. Surfactant-containing hair shampoo and body cleansing agent the surfactant component of which consists essentially of an alkylsulfatobetaine of the formula

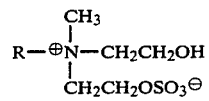

wherein R is coconut fatty alkyl.

2. A cleansing agent according to claim 1, in powder, gel or liquid form, which contains 5–20% by weight of the powder, gel or liquid of said alkylsulfatobetaine.

3. A cleansing agent according to claim 2, the surfactant component of which includes anionic, cationic, nonionic, and other amphoteric surfactants, or mixtures thereof.

4. A shampoo and body cleansing agent comprising 1–50% by weight of an alkylsulfatobetaine of the formula

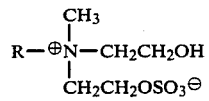

wherein R is coconut fatty alkyl.

* * * * *